United States Patent
Kinoshita

(10) Patent No.: US 9,271,655 B2
(45) Date of Patent: Mar. 1, 2016

(54) OSCILLOMETRIC TYPE SPHYGMOMANOMETER

(71) Applicant: Hiroyuki Kinoshita, Kyoto (JP)

(72) Inventor: Hiroyuki Kinoshita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 387 days.

(21) Appl. No.: 13/766,856

(22) Filed: Feb. 14, 2013

(65) Prior Publication Data

US 2013/0226012 A1    Aug. 29, 2013

(30) Foreign Application Priority Data

Feb. 24, 2012    (JP) .................................. 2012-038933

(51) Int. Cl.
    *A61B 5/021*    (2006.01)
    *A61B 5/022*    (2006.01)
    *A61B 5/0225*   (2006.01)
    *A61B 5/024*    (2006.01)

(52) U.S. Cl.
    CPC ........... *A61B 5/02108* (2013.01); *A61B 5/0225* (2013.01); *A61B 5/02225* (2013.01); *A61B 5/024* (2013.01)

(58) Field of Classification Search
    CPC ........... A61B 5/02108; A61B 5/02225; A61B 5/0225; A61B 5/024; A61B 5/02233; A61B 5/205; A61B 8/04
    See application file for complete search history.

(56) References Cited

FOREIGN PATENT DOCUMENTS

| JP | 03-055026 A | 3/1991 |
|----|-------------|--------|
| JP | 9-055026 A  | 2/1997 |
| JP | 09-253059 A | 9/1997 |
| JP | 2002-209859 A | 7/2002 |

OTHER PUBLICATIONS

Patent Abstracts of Japan, Publication No. 09-055026, Published on Feb. 25, 1997, 1 page.
Patent Abstracts of Japan, Publication No. 03-055026, Published on Mar. 8, 1991, 1 page.
Patent Abstracts of Japan, Publication No. 2002-209859, Published on Jul. 30, 2002, 1 page.

*Primary Examiner* — Christine H Matthews
(74) *Attorney, Agent, or Firm* — Osha Liang LLP

(57) ABSTRACT

A sphygmomanometer includes a pulse wave detecting section, a pulse wave amplitude calculation section, a pace change calculation section, and a pulse wave amplitude correction section. The pulse wave detecting section detects pulse waves, and the pulse wave amplitude calculation section calculates an amplitude of a pulse wave. The pace change calculation section calculates the amount of change of the increasing/decreasing pace of the cuff pressure between pulse waves based on the difference between the increasing/decreasing pace of the cuff pressure during a period of the pulse wave and the increasing/decreasing pace of the cuff pressure during a period of a preceding pulse wave. The pulse wave amplitude correction section corrects the amplitude of the pulse wave based on the amount of change of the increasing/decreasing pace of the cuff pressure. A blood pressure value is determined based on the corrected amplitude of the pulse wave.

8 Claims, 12 Drawing Sheets

OSCILLOMETRIC TYPE SPHYGMOMANOMETER

BACKGROUND OF THE INVENTION

1. Field of the Invention

The present invention relates to an oscillometric type blood pressure measurement device, a blood pressure measurement method and a blood pressure measurement program.

2. Description of the Related Art

An oscillometric type blood pressure measurement device as a device that automatically measures a blood pressure value of a living body is known (refer to Japanese Unexamined Patent Application No. H09-253059, Japanese Unexamined Patent Application No. H03-55026, and Japanese Unexamined Patent Application No. 2002-209859.)

An oscillometric type automated blood pressure measurement device gradually changes a compression on a living body through a cuff wrapped around one part of the living body at a predetermined pace and, at the same time, detects cuff pressure during a period of this change in compression. Then, from the detected cuff pressure, the oscillometric type automated blood pressure measurement device detects a pulse wave that is a pressure component synchronized with a pulse of the living body and superimposed on the compression, and determines the blood pressure value of the living body based on a change in amplitude of that pulse wave.

FIG. 10 is a diagram illustrating a change in detected cuff pressure in a period where the cuff is being inflated by a basic oscillometric type blood pressure measurement device. In FIG. 10, a horizontal axis represents time and a vertical axis represents detected cuff pressure.

A straight line illustrated by a broken line of FIG. 10 illustrates compression from the cuff (inflation base line), and the example of FIG. 10 illustrates a case where compression is increasing at a constant pace from the cuff inflation start. A solid line of FIG. 10 illustrating each mountain-shaped wave form is illustrating a pulse wave superimposed on the compression illustrated by a broken line.

Various ways are known for calculating an amplitude value of a pulse wave needed to determine a blood pressure value. For example, in FIG. 10, if a difference between a peak value of the pulse wave and the pressure, on a straight line connecting rising points of the pulse wave, at a time when the peak value is obtained (a1, a2 and a3 in FIG. 10) is calculated as a pulse wave amplitude, the blood pressure value can be determined with high accuracy.

The blood pressure measurement devices disclosed in the Japanese Unexamined Patent Applications do not obtain amplitude value by the aforementioned method, but they do perform a variety of innovations to raise a measurement accuracy of the blood pressure value.

The blood pressure measurement device of Japanese Unexamined Patent Application No. H09-253059 measures a change pace of a compression of the cuff at a time of pulse wave generation and raises the measurement accuracy of the blood pressure value by correcting the compression at the time of pulse wave generation according to this pace.

The blood pressure measurement device of Japanese Unexamined Patent Application No. H03-55026 raises the measurement accuracy of the blood pressure value by correcting an error in the blood pressure value that is subject to a pulse rate.

The blood pressure measurement device of Japanese Unexamined Patent Application No. 2002-209859 raises the measurement accuracy of the blood pressure value by correcting pulse wave amplitude based on a photoelectric pulse wave detected from a photoelectric pulse wave sensor, correcting the compression based on a heartbeat period and determining maximum and minimum blood pressure values from post-correction pulse wave amplitude and pressure.

Control to increase a compression from a cuff at a constant pace is performed in an oscillometric type blood pressure measurement device in order to detect an amplitude value of a pulse wave with precision, as illustrated in FIG. 10.

Sphygmomanometers for home use have become more prevalent in recent years, but from a perspective of improving usability of sphygmomanometers for home use, miniaturization and cost reduction are demanded. Because of that, cost reduction and miniaturization of a pump that sends fluid to a cuff have advanced.

However, because pump size and cost have a mutual trade off relationship with output flow rate, it becomes increasingly difficult to achieve a desired inflation pace as miniaturization and cost reduction advance.

FIG. 11 illustrates a state where a change pace of the compression in FIG. 10 changes in midstream. FIG. 11 illustrates a state of a time when the change pace of the compression of the cuff up to time t1 and the change pace of the compression of the cuff after time t2 change.

In this state, the compression of the cuff between time t1 and time t2 changes to a curved condition as shown by a dashed line, and the compression of the cuff is not changing in a constant manner. Accordingly, when amplitude a2 of the pulse wave is determined through the aforementioned method, an error is generated in relation to a precise amplitude a2', and measuring accuracy of a blood pressure value decreases.

The blood pressure measurement devices disclosed in Patent Documents 1-3 do not calculate a difference between a peak value of the pulse wave and a pressure, on a straight line connecting rising points of the pulse wave, at a time when the peak value is obtained as a pulse wave amplitude value. Because of that, a situation where the compression of the cuff is not changing in a constant manner does not occur with Patent Documents 1-3 and, not surprisingly, this situation is not considered in Patent Documents 1-3.

Accordingly, one or more embodiments of the present invention provides a blood pressure measurement device, a blood pressure measurement method and a blood pressure measurement program that are capable of performing measurement of blood pressure value with high accuracy.

SUMMARY OF THE INVENTION

One or more embodiments of the present invention relates to an oscillometric type sphygmomanometer, comprising: a cuff for wrapping around a measurement location of a patient; a pump and valve for inflating/deflating the cuff; a pressure sensor for measuring a cuff pressure on the measurement location during inflation/deflation of the cuff; a central control unit stored in a body of the sphygmomanometer for controlling measurement of blood pressure, the central control unit comprising: a memory storing a program and data to enable the central control unit to perform a predetermined operation; a cuff pressure detection section for receiving a cuff pressure measured by the pressure sensor; a discrimination section for detecting pulse waves that are synchronized with a pulse rate of the patient and superimposed on the cuff pressure; a pulse rate calculation section for calculating the pulse rate based on an interval between the pulse waves detected by the discrimination section; a pulse wave amplitude calculation section that: detects a rising time $t_0$ of a pulse wave, a rising time $t_1$ of a following pulse wave, and cuff pressure t0p and cuff pressure t1p at the rising times t0 and t1 respectively, detects a time ta when the pulse wave reaches a peak between time t0 and t1 and a cuff pressure M1 at the time ta, draws a straight line between (t0, t0p) and (t1, t1p) on an x-y coordinate system in which x coordinate represents time and y coordinate represents cuff pressure value, and determines a position coordinate (ta, M2) on the straight line; calculates amplitude of the pulse wave between time t0 and t1 based on the difference between M1 and M2, a pace change calculation section for calculating amount of change of increasing/decreasing pace of cuff pressure between the pulse waves based on the difference between increasing/decreasing pace of the cuff pressure during a period of the pulse wave and increasing/decreasing pace of the cuff pressure during a period of a preceding pulse wave; a pulse wave amplitude correction section for correcting the amplitude of pulse wave based on the amount of change of increasing/decreasing pace of the cuff pressure calculated by the pace change calculation section and the pulse rate calculated by the pulse rate calculation section in accordance with a predetermined method; and a blood pressure determination section for determining a blood pressure value based on the amplitude of the pulse wave corrected by the pulse wave amplitude correction section.

According to one or more embodiments of the present invention, the memory stores a threshold value of amount of change of increasing/decreasing pace, and the pulse wave amplitude correction section corrects the amplitude of pulse wave only when amount of change of increasing/decreasing pace of cuff pressure exceeds the threshold value between the pulse waves.

According to one or more embodiments of the present invention, the pressure sensor is a capacitive type pressure sensor.

According to one or more embodiments of the present invention, the discrimination section detects pulse wave that is synchronized with pulse rate of a patient and superimposed on the cuff pressure by a filter processing.

According to one or more embodiments of the present invention, the pulse wave amplitude correction section corrects the amplitude of pulse wave based on the amplitude error calculated in accordance with the following formula: Amplitude error=($\alpha$× pulse rate+$\beta$)×change amount of pace, in which $\alpha$ represents a coefficient experimentally obtained from the relationship between a value obtained by deducting amplitude error from increasing/decreasing pace of cuff pressure and pulse rate, and $\beta$ represents a value obtained by deducting amplitude error from increasing/decreasing pace of cuff pressure at a minimum pulse rate.

According to one or more embodiments of the present invention, the pace change calculation section detects cuff pressure during each pulse wave by sampling pulse waves at predetermined time intervals and calculates increasing/decreasing pace of the cuff pressure at the time intervals, and calculates mean value of increasing/decreasing pace of the cuff pressure as an increasing/decreasing pace of the cuff pressure during the period of the pulse waves.

One or more embodiments of the present invention relate to a method of measuring a blood pressure by using an oscillometric type sphygmomanometer, comprising: wrapping a cuff comprising a pressure sensor around a measurement location of a patient; inflating and deflating the cuff; detecting a cuff pressure on the measurement location during inflation/deflation of the cuff; detecting pulse wave that is synchronized with pulse rate of a patient and superimposed on the cuff pressure; calculating pulse rate based on an interval between the detected pulse waves; detecting a rising time t0 of a pulse wave, a rising time t1 of a following pulse wave, and cuff pressure t0p and t1p at the rising time t0 and t1, and detecting time ta when the cuff pressure of the pulse wave reaches a peak between t0 and t1 and a cuff pressure M1 at the time ta, drawing a straight line between (t0, t0p) and (t1, t1p) on a x-y coordinate system in which x coordinate represents time and y coordinate represents cuff pressure value, and determining a position coordinate (ta, M2) on the straight line, calculating amplitude of the pulse wave based on the difference between M1 and M2 on the straight line, calculating amount of change of increasing/decreasing pace of cuff pressure between the pulse waves based on the difference between increasing/decreasing pace of the cuff pressure during a period of the pulse wave and increasing/decreasing pace of the cuff pressure during a period of a preceding pulse wave; correcting the amplitude of pulse wave based on the amount of the detected increasing/decreasing pace of the cuff pressure and pulse rate in accordance with a predetermined method; and determining blood pressure value based on the corrected amplitude of the pulse wave.

According to one or more embodiments of the present invention, the pulse wave amplitude correction section corrects the amplitude of pulse wave only when amount of change of increasing/decreasing pace of cuff pressure exceeds a predetermined threshold value between the pulse waves.

One or more embodiments of the present invention relate to a recording medium storing the steps of: wrapping a cuff comprising a pressure sensor around a measurement location of a patient; inflating and deflating the cuff; detecting a cuff pressure on the measurement location during inflation and/or deflation of the cuff; detecting pulse wave that is synchronized with pulse rate of a patient and superimposed on the cuff pressure; calculating pulse rate based on an interval between the detected pulse waves; detecting a rising time t0 of a pulse wave, a rising time t1 of a following pulse wave, and cuff pressure t0p and t1p at the rising time t0 and t1, and detecting time ta when the cuff pressure of the pulse wave reaches a peak between t0 and t1 and a cuff pressure M1 at the time ta, drawing a straight line between (t0, t0p) and (t1, t1p) on a x-y coordinate system in which x coordinate represents time and y coordinate represents cuff pressure value, and determining a position coordinate (ta, M2) on the straight line, calculating amplitude of the pulse wave based on the difference between M1 and M2 on the straight line, calculating amount of change of increasing/decreasing pace of cuff pressure between the pulse waves based on the difference between increasing/decreasing pace of the cuff pressure during a period of the pulse wave and increasing/decreasing pace of the cuff pressure during a period of a preceding pulse wave; correcting the amplitude of pulse wave based on the amount of the detected increasing/decreasing pace of the cuff pressure and pulse rate in accordance with a predetermined method; and determining blood pressure value based on the corrected amplitude of the pulse wave.

DETAILED DESCRIPTION OF INVENTION

Embodiments of the present invention will be described hereinafter with reference to figures.

Figure 1:
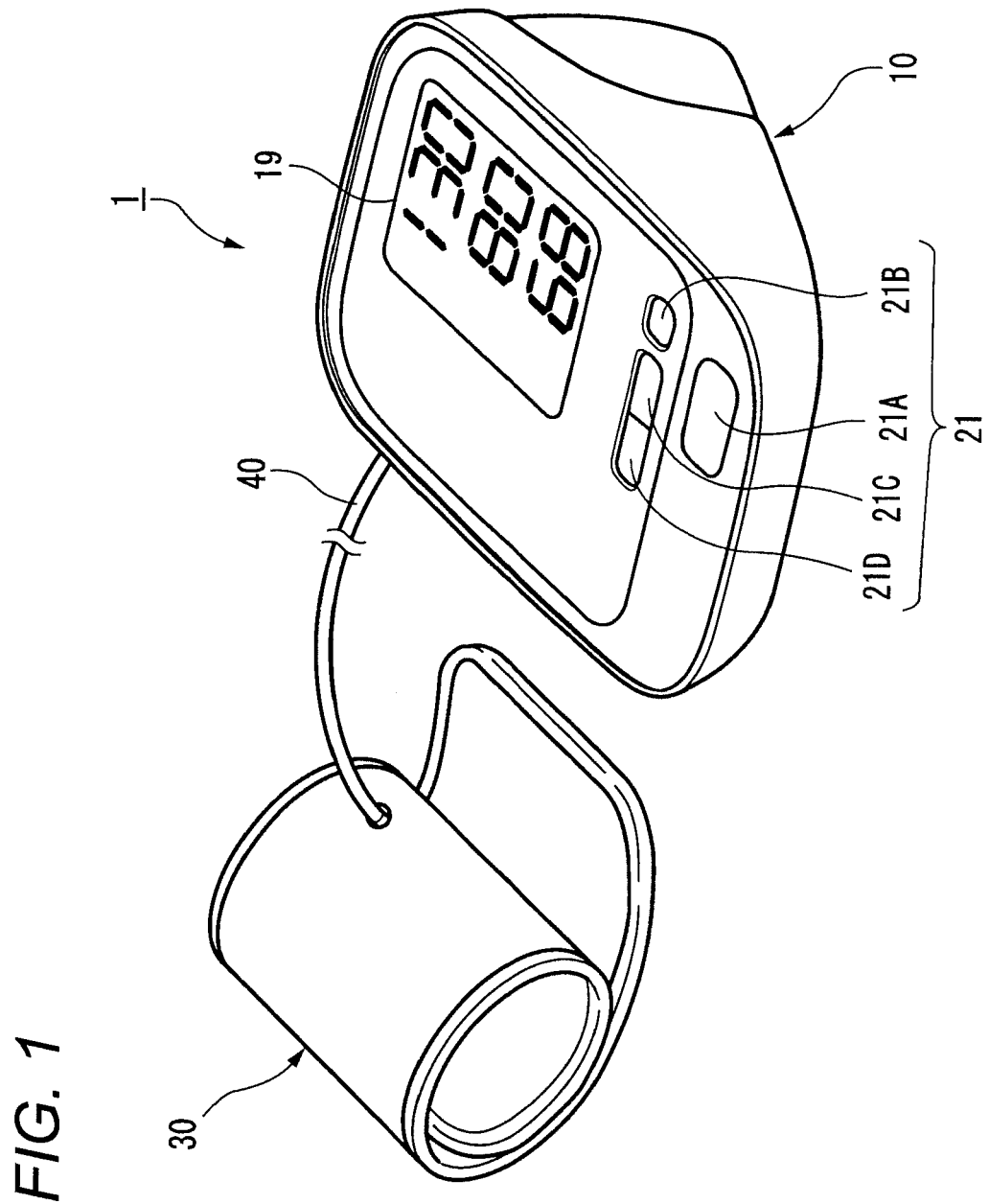
FIG. 1 is a diagram illustrating an outer appearance of a schematic configuration of a blood pressure measurement device in order to describe one embodiment of the present invention.

FIG. 1 is a diagram illustrating an outer appearance of a schematic configuration of a blood pressure measurement device in order to describe one embodiment of the present invention.

A blood pressure measurement device 1 has a main body part 10, a cuff 30 capable of wrapping around an upper arm of a measurement subject, and an air tube 40 for connecting the main body part 10 and the cuff 30.

The cuff, in this specification, means a bandlike or cylindrical structure having a lumen that is capable of wrapping around a measurement location of a living body (for example, an upper au or a wrist and the like) and is used to compress an artery and measure a blood pressure of a measurement subject through injecting a fluid of gas or liquid and the like into the lumen.

Cuff is a word that illustrates a concept that includes a fluid bag and a wrapping around means for wrapping the fluid bag around a living body and that is also referred to as an arm band. In an example in FIG. 1, the cuff 30 and the main body part 10 are separate, but the cuff 30 and the main body part 10 may be integrated.

The main body part 10 has a display part 19 configured from, for example, a liquid crystal and the like for displaying a variety of information such as blood pressure value, pulse rate, and the like, and an operation part 21 including a plurality of switches 21A, 21B, 21C and 21D for receiving instruction from a user (measurement subject).

The operation part 21 has measure/stop switch 21A that receives input of instructions to turn power supply ON or OFF and instructions to start and stop measurement, memory switch 21B for reading information of blood pressure and the like recorded in the main body part 10 and receiving instructions for the display thereof on the display part 19, and arrow switches 21C and 21D and the like for receiving instruction for lowering or raising memory number at the time information is called.

Figure 2:
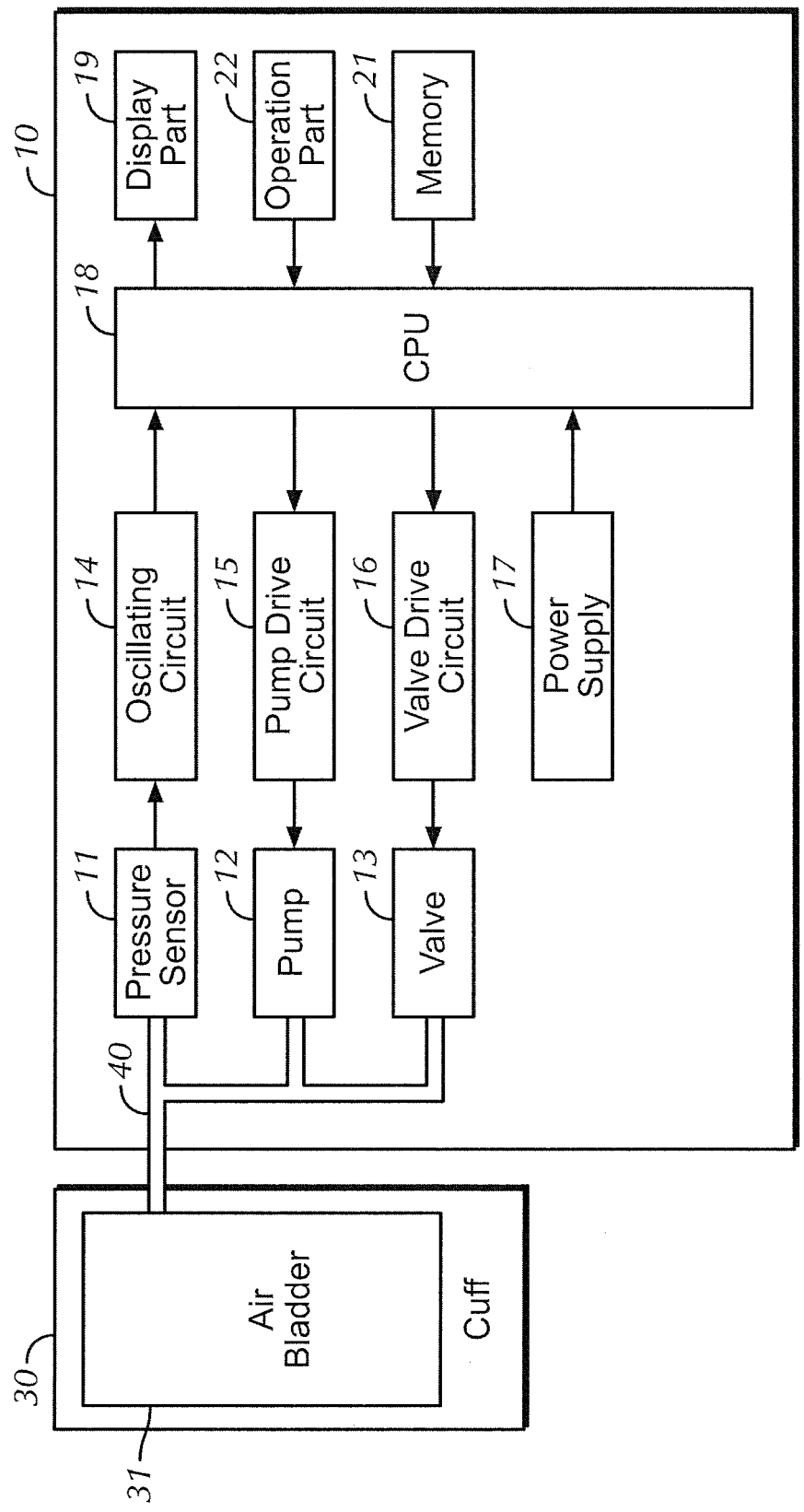
FIG. 2 is a diagram illustrating an internal configuration of the blood pressure measurement device 1 illustrated in FIG. 1.

FIG. 2 is a diagram illustrating an internal configuration of the main body part 10 in the blood pressure measurement device 1 illustrated in FIG. 1

The cuff 30 includes an air bladder 31 and the air tube 40, illustrated in FIG. 1, is connected to this air bladder 31.

The main body part 10 has a pressure sensor 11, pump 12 and exhaust valve (hereinafter called, valve) 13 connected to the air tube 40, an oscillating circuit 14, a pump drive circuit 15, a valve drive circuit 16, a power supply 17 that supplies power to all parts of the main body part 10, the display part 19 illustrated in FIG. 1, a controller (CPU) 18 that controls the entire main body part 10 and performs a variety of operations, the operation part 21 and a memory 22.

The pump 12 supplies air to the air bladder 31 in order to increase compression on a measurement location through the cuff 30.

The valve 13 opens and closes in order to exhaust or include air out of or into the air bladder 31.

The pump drive circuit 15 controls the driving of pump 12 based on a control signal received from the CPU 18.

The valve drive circuit 16 performs the opening and closing control of valve 13 based on a control signal received from the CPU 18.

A compression adjustment part that changes the compression on the measurement location from the cuff 30 is configured from the pump 12, the valve 13, the pump drive circuit 15 and the valve drive circuit 16.

As one example, the pressure sensor 11 uses a capacitive type sensor. The capacitive type sensor changes capacitance value according to pressure detected thereby.

The oscillating circuit 14 oscillates based on the capacitance value of the pressure sensor 11 and outputs a signal based on the capacitance value to the CPU 18. The CPU 18, by converting the signal output from the oscillating circuit 14 to a pressure value, detects the pressure of the cuff 30 (cuff pressure).

The memory 22 includes Read Only Memory (ROM) that records data and a program for operating a prescribed program in the CPU 18, Random Access Memory (RAM) as working memory and flash memory that stores measured blood pressure data and the like.

Figure 3:
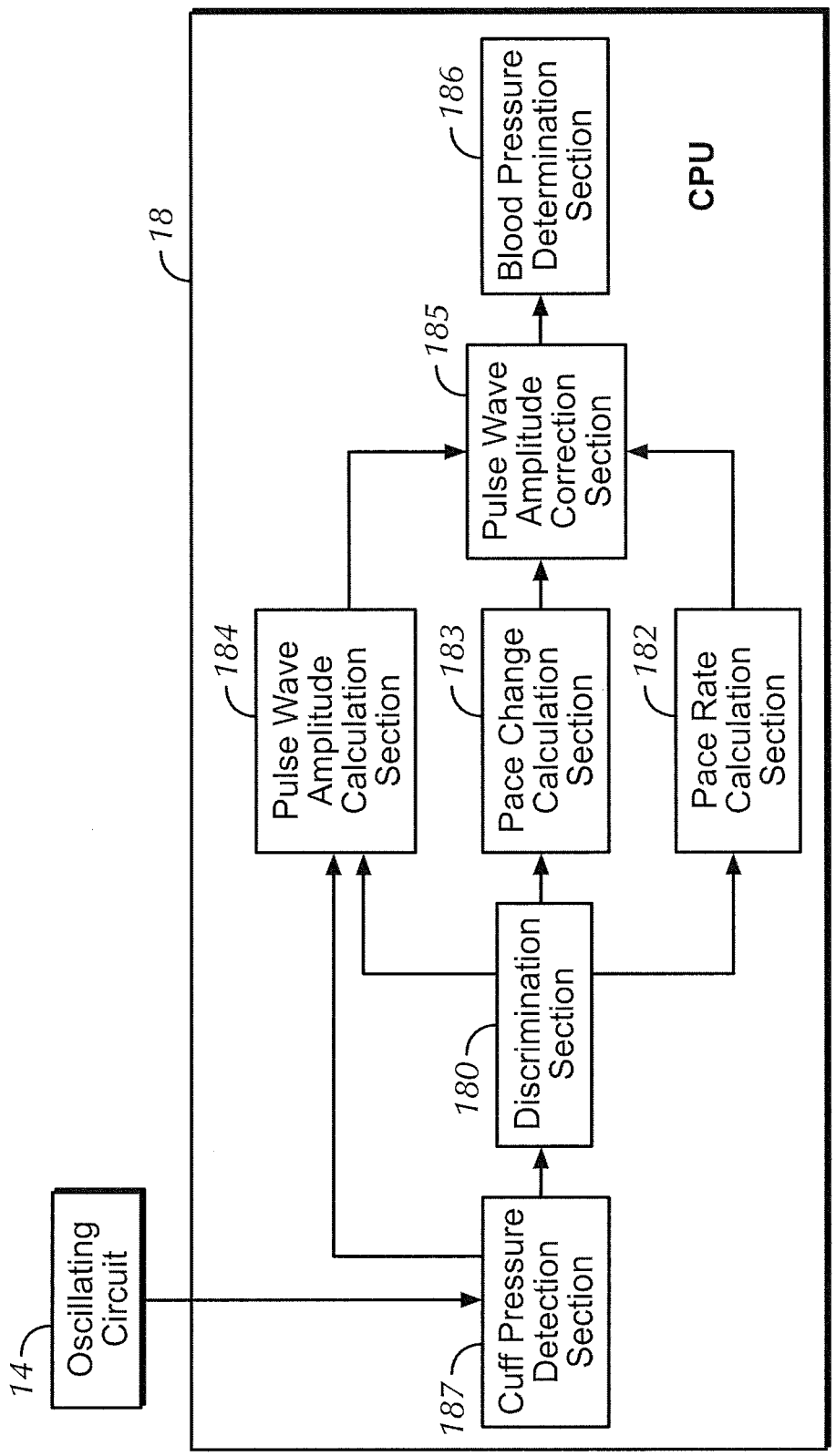
FIG. 3 is a function block diagram realized through a CPU 18, illustrated in FIG. 2, reading and executing a program recorded in ROM.

FIG. 3 is a function block diagram realized through a CPU 18, illustrated in FIG. 2, reading and executing a blood pressure measurement program recorded in ROM.

The CPU 18 has a cuff pressure detection section 187, a discrimination section 180, a pulse rate calculation section 182, a pace change calculation section 183, a pulse wave amplitude calculation section 184, a pulse wave amplitude correction section 185 and a blood pressure determination section 186.

These are functions formed mainly in the CPU 18 by the CPU 18 reading and executing a program recorded in the memory 22, but one or all of these functions may be formed by a hardware configuration.

The cuff pressure detection section 187 converts the output signal of the oscillating circuit 14 to a pressure value and detects the cuff pressure.

Through filter processing, for example, the discrimination section 180 detects steady pressure, that is, the compression from the cuff 30 from the cuff pressure detected through the cuff pressure detection section 187, and a pulse wave that is a pressure component superimposed on the compression, which is synchronized with the pulse of the living body.

The pulse rate calculation section 182 calculates pulse rate based on the pulse wave detected through the discrimination section 180. Specifically, with Tpw representing an interval of the pulse wave detected through the discrimination section 180 (a time period from a rising point of a pulse wave to the rising point of a following pulse wave), the pulse rate calculation section 182 detects pulse rate PLS through the equation below.

$$PLS=60/Tpw \quad [1]$$

The pace change calculation section 183 calculates pace change, which is a difference between the change pace during the period of the pulse wave in each pulse wave detected through the discrimination section 180 based on the compression detected through the discrimination section 180 and the change pace of the compression during the period of the pulse wave of the preceding pulse wave.

Specifically, the pace change calculation section 183 does sampling of compression during the period of each pulse wave detected through the discrimination section 180 at a prescribed interval, calculates the change pace for each sampling interval and calculates the average of the calculated change pace as the change pace of the compression during the period of the pulse wave.

The pulse wave amplitude calculation section 184 analyzes cuff pressure detected through the cuff pressure detection section 187 and calculates amplitude of the pulse wave.

The pulse wave amplitude calculation section 184, in relation to the cuff pressure detected through the cuff pressure detection section 187, sets a straight line tying a pressure value during a rising timing of a pulse wave detected through the discrimination section 180 to a pressure value during the rising timing of a pulse wave following the pulse wave. Then, it calculates the difference between the pulse wave peak value and the pressure value on the straight line during the point in time that the peak value is obtained as the amplitude value of the pulse wave.

Figure 11:
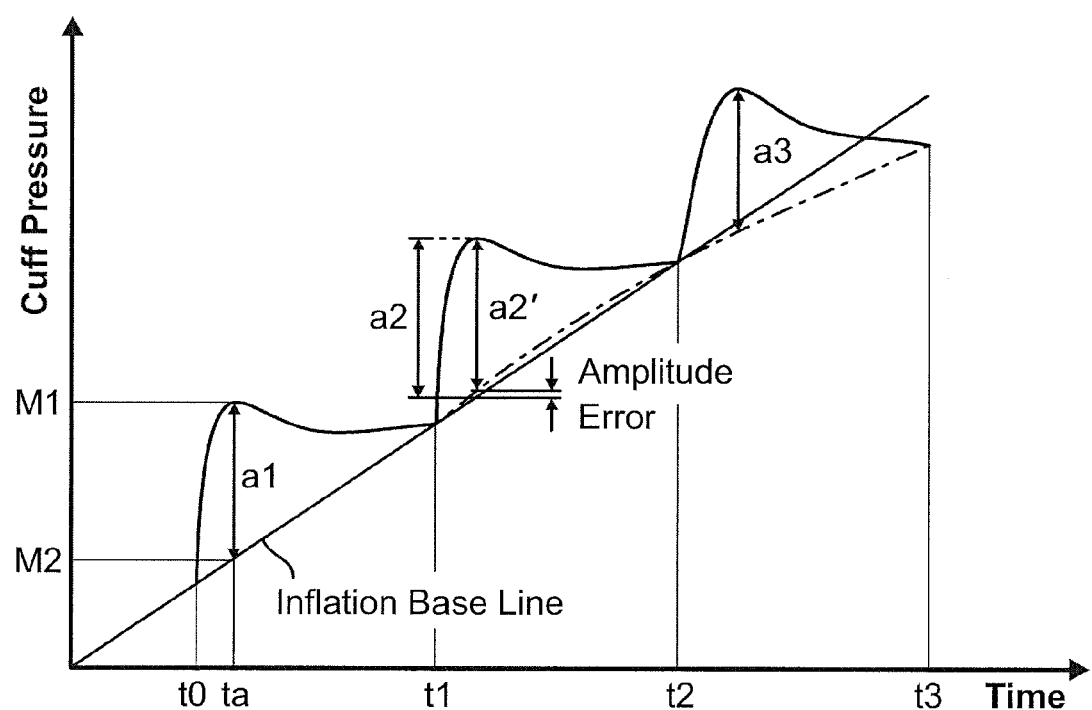
FIG. 11 is a diagram illustrating a state when a change pace of the compression in FIG. 10 changes in midstream.

Specifically, with reference to FIG. 11, the cuff pressure detection section 187 detects the point in time of the rising of each pulse wave and the cuff pressure. In the first pulse wave illustrated in FIG. 11, the pulse wave amplitude calculation section 184 detects pulse wave rising time t0, a following rising time t1, and a maximum value of the pressure value in a period between t0 and t1 (peak value of the pulse occurring in the period) M1 and time ta at generation thereof. Subsequently, the pulse wave amplitude calculation section 184 draws a straight line connecting a coordinate point illustrating time t0 and a cuff pressure value at that point in time with a coordinate point illustrating time t1 and a cuff pressure at that point in time and calculates pressure value M2 on the line at time ta where the peak value of the pulse wave was obtained. Because this value M2 can be thought of as equal to the compression applied steadily to the measurement location by the cuff without regard to the pulse wave, by deducting the value of M2 from the value of cuff pressure M1 at the peak time of the pulse wave, amplitude of the pulse wave generated between time t0 and time t1 can be calculated. The pulse wave amplitude calculation section 184 performs the same operation each time the discrimination section 180 detects a pulse wave and calculates amplitude.

The pulse wave amplitude correction section 185 corrects the amplitude calculated through the pulse wave amplitude calculation section 184 based on the pace change amount and the pulse rate.

The blood pressure determination section 186 determines the blood pressure value through a well-known method using the amplitude of a pulse wave output from the pulse wave amplitude correction section 185.

As previously mentioned, the amplitude of the pulse wave calculated through the pulse wave amplitude calculation section 184 will generate an error in relation to a precise amplitude when the change pace of the compression of the cuff 30 during the period of that pulse wave is not constant.

With that, the blood pressure measurement device 1 of this embodiment records correction data in the memory 22 of the main body part 10 in order to correct the error.

Figure 4:
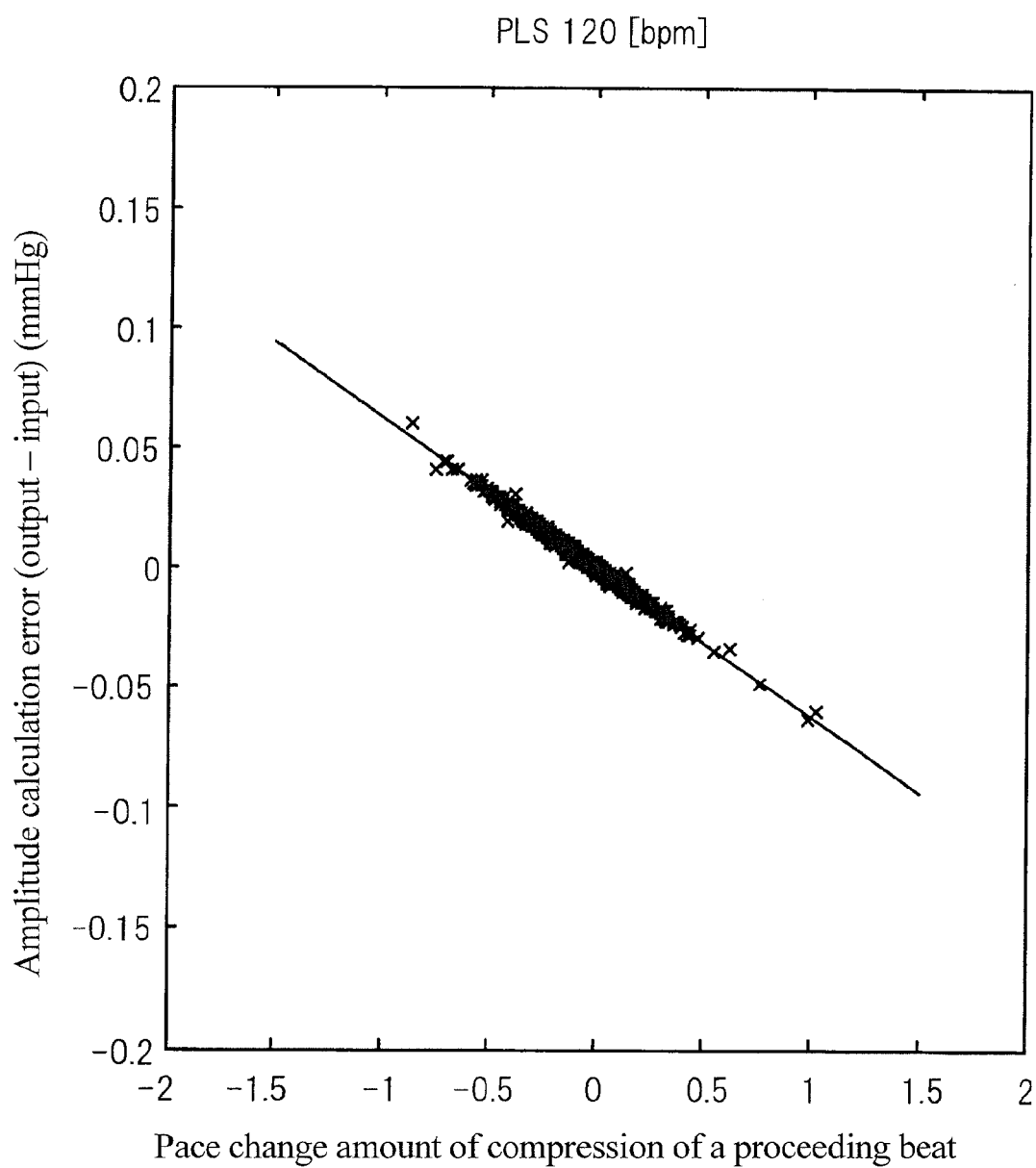
FIG. 4 is a graph illustrating the examined results of a relationship between an error in amplitude of a pulse wave and a change in relation to a preceding pulse wave of a change pace of a compression during a period of the pulse wave.

FIG. 4 is a graph illustrating the examined results of a relationship between an error in amplitude of the pulse wave and the pace change amount, which is the difference between the change pace of the compression during the period of the pulse wave of a pulse wave preceding the pulse wave and the change pace of the compression during the period of the pulse wave.

FIG. 4 illustrates, in relation to a plurality of pulse waves with known amplitudes (pulse rate: 120 (bpm)), the value of deducting the known amplitude from a result of calculating amplitude by a calculation method through the pulse wave amplitude calculation section 184 as an amplitude calculation error on the vertical axis. FIG. 4 also illustrates the compression pace change amount in relation to the preceding pulse wave (preceding beat) of every pulse wave on the horizontal axis.

As illustrated in FIG. 4, if the pace change amount of the compression (absolute value ignoring sign) is zero, amplitude error does not occur, and the larger the pace change amount becomes, the larger a calculation error of the amplitude becomes. Through this, it is understood that the pace change amount of the compression and the error in amplitude are correlated.

Note that FIG. 4 is data examined for the pulse wave superimposed on compression in a process where the compression of the cuff increases that also illustrates the same relationship for the data of the pulse wave superimposed on compression in a process where the compression of the cuff is reduced.

Figure 5:
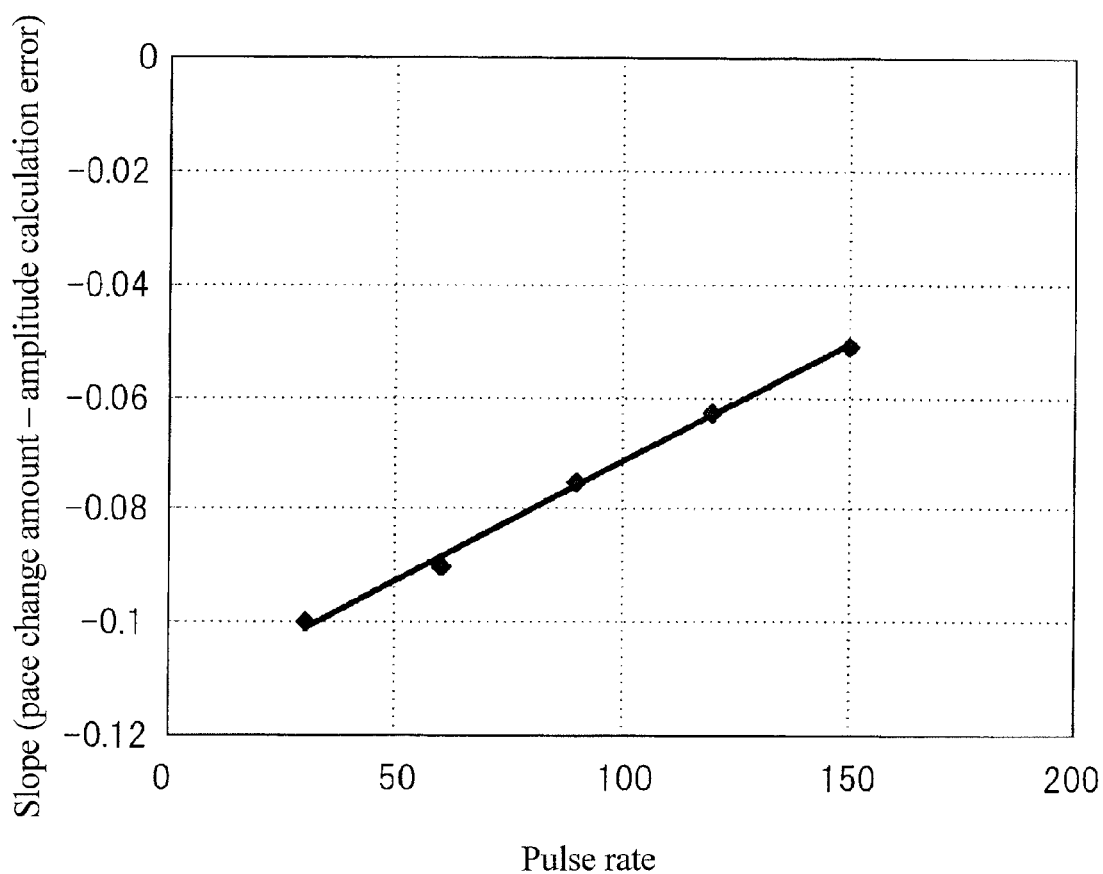
FIG. 5 is a graph illustrating results obtained by changing data illustrated in FIG. 4 to pulse rate.

FIG. 5 is a graph illustrating results obtained by changing data illustrated in FIG. 4 to pulse rate. In FIG. 5, a slope of a function showing the pace change amount of the compression of the cuff and the error in amplitude is illustrated on the vertical axis, and the pulse rate is illustrated on the horizontal axis.

As illustrated in FIG. 5, as pulse rate increases, the slope of the function showing the pace change amount of the compression of the cuff and the error in amplitude decreases. The reason for a result like this is thought to be due to a width of a temporal axis of the pulse wave getting smaller when pulse rate is high, to a result that a curved portion of an inflation base line during the period of the pulse wave, as illustrated in FIG. 11, approaches relatively close to the straight line and to the amplitude error becoming smaller.

The data illustrated in FIG. 4 and FIG. 5 is recorded as correction data in the memory 22 of the main body part 10. Note that, a method for holding this correction data may be the holding thereof as a table corresponding to vertical axis data and horizontal axis data and may also be held as data of a function showing a straight line illustrated in FIG. 4 and FIG. 5.

Below, an example of a case of holding correction data as a function is given. Note that the function for showing the straight line illustrated in FIG. 4 is y=γx, and the function for showing the straight line illustrated in FIG. 5 is y=αx+β.

The pulse wave amplitude correction section 185 calculates the error in amplitude AmpErr of the pulse wave through the operation of the equation (2) below.

$$AmpErr=\gamma \times \Delta V=(\alpha \times PLS+\beta) \times \Delta V \quad (2)$$

In equation (2), α illustrates the slope of the function showing the data illustrated in FIG. 5, and β illustrates a segment of the function showing the data illustrated in FIG. 5. Also, ΔV illustrates the pace change amount calculated through the pace change calculation section 183.

The pulse wave amplitude correction section 185 performs correction of the amplitude by adding an error AmpErr calculated in this way to the amplitude calculated through the pulse wave amplitude calculation section 184.

A description of the operation of a blood pressure measurement device 1 configured as above is given below.

Figure 6A:
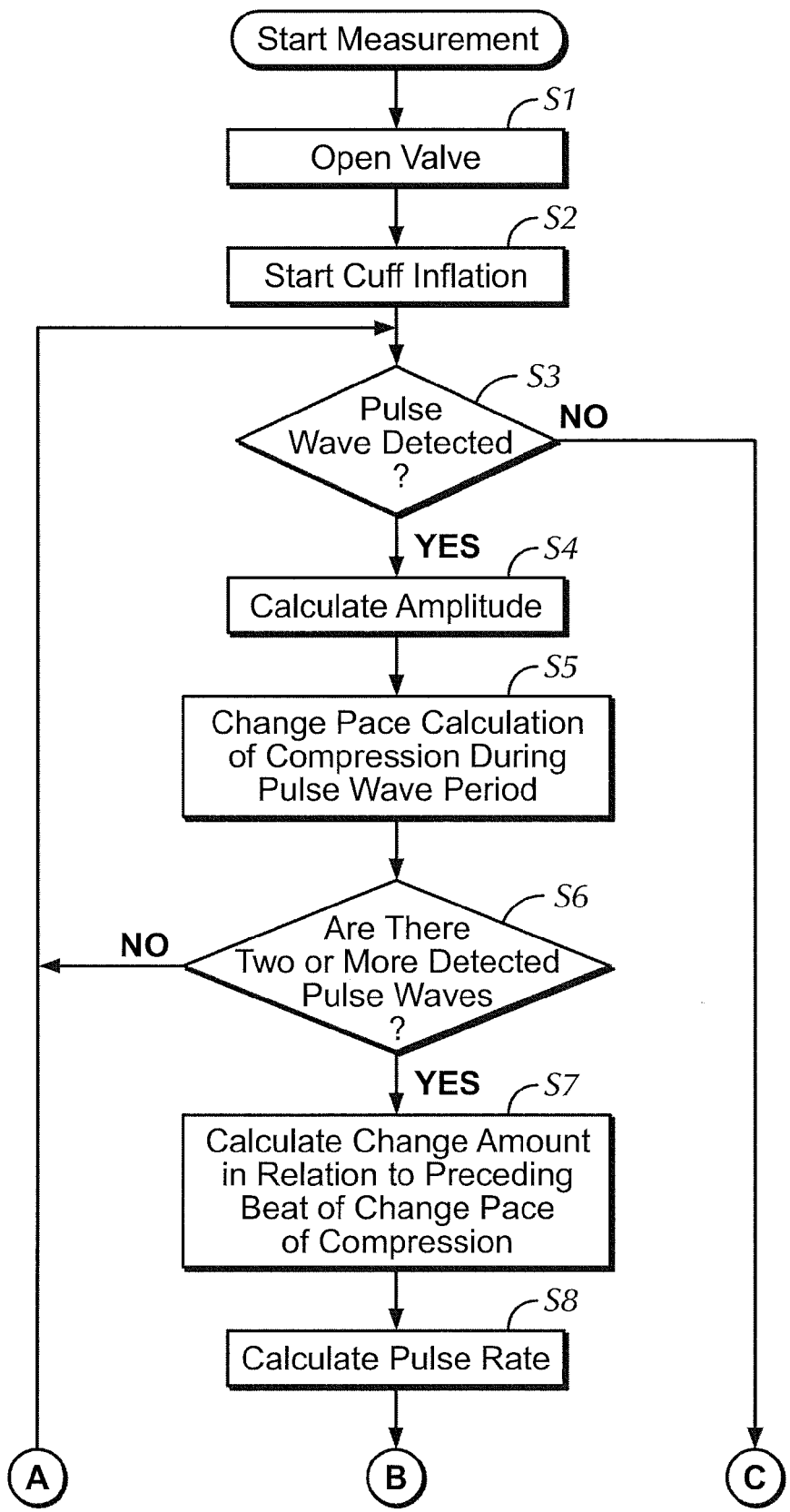
FIGS. 6A and 6B are a flow chart to describe an operation of the blood pressure measurement device illustrated in FIG. 1.
Figure 6B:
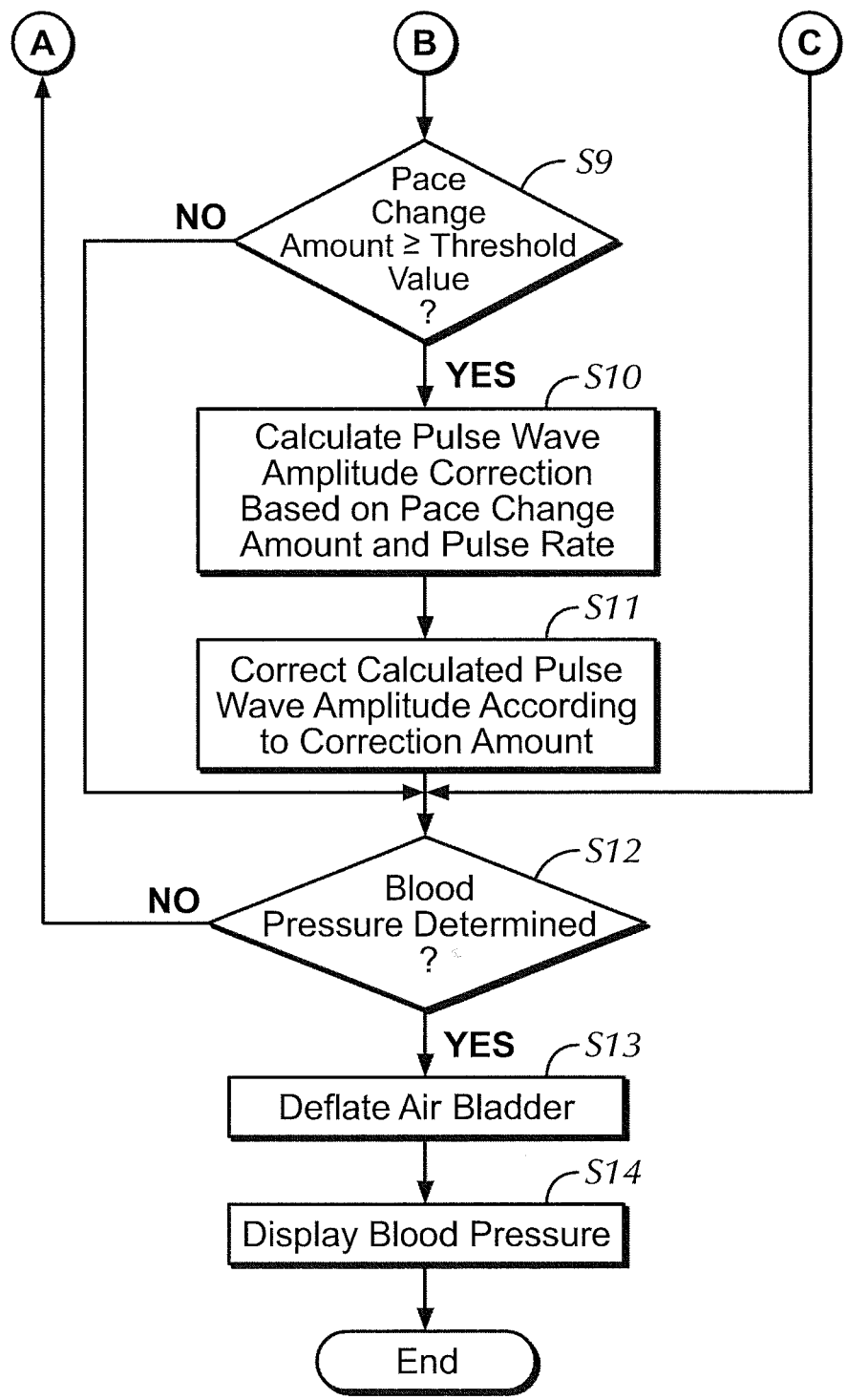

FIGS. 6A and 6B are a flow chart to describe an operation of the blood pressure measurement device 1 illustrated in FIG. 1.

When start of measurement of blood pressure is instructed through pushing the measure/stop switch 21A, the CPU 18 opens the valve 13 (step S1) and starts inflation of the cuff 30 by infusing air into cuff 30 through the pump 12 (step 2).

When a pulse wave is detected after start of the inflation of cuff 30 (step S3: YES), the CPU 18 calculates amplitude for that detected pulse wave (step S4).

Next, the CPU 18 calculates the change pace of the compression during the period of the pulse wave (step S5).

Next, the CPU 18, in the case that two or more pulse waves are being detected thereby (step S6: YES), performs processing of step S7. In the case that only one pulse wave is being detected (step 6: NO), returns processing to step S3.

In step S7, the CPU 18 calculates a difference between the change pace of the compression calculated in relation to the newest detected pulse wave and the change pace of the compression calculated in relation to the pulse wave preceding the detected pulse wave as the pace change amount of the compression during the period of the newest detected pulse wave.

Next, the CPU 18 calculates the pulse rate PLS based on the newest detected pulse wave (step S8).

Next, if the pace change amount detected in step S7 (absolute value ignoring sign) is above a threshold value, the CPU 18 performs processing of step S1.

This threshold value is a threshold value for the purpose of determining whether or not to correct the amplitude value calculated in step S4. As is made clear by data illustrated in FIG. 4, amplitude correction is not necessary if the pace change amount of the compression is zero. However, because some degree of variance occurs in the pace change amount detected in step S7, with consideration for this variance at this point, the threshold value is set as a value slightly larger than zero.

In step 10, the CPU 18 performs the operation of equation (2) from the pace change amount calculated in step S7, the pulse rate calculated in step S8, and the function data of FIG. 4 and FIG. 5 recorded in the memory 22, and calculates the error in amplitude (correction amount).

In the case where the pace change amount is below the threshold value in step S9, because it can be determined that there is no error in the amplitude calculated in step S4, the CPU 18 performs the processing of step S12 without performing the processing of step S10 or step S11.

In step S12, the CPU 18 determines blood pressure using the amplitude in relation to each pulse wave (the value after correction in the case that step S10 and Step S11 were performed).

The CPU 18 returns to the processing of step S3 in the case that an amplitude sampling number does not reach a number capable of determining the blood pressure value (step 12: NO).

Upon determining blood pressure in step S12, the CPU 18 stops inflation through the pump 12, opens the valve 13, and performs deflation of the air bladder 31 (step S13).

Then, the CPU 18 displays the blood pressure value determined in step S12 on the display part 19 (step S14) and completes a blood pressure measurement process.

As above, with the blood pressure measurement device 1 of this embodiment, without the change pace of the compression through the cuff 30 during the pulse wave period being constant, even in the case where an error is included in the amplitude calculated in step S4, this error can be corrected based on the pace change amount of the compression and the pulse rate. Because of this, the amplitude of the pulse wave can be detected with precision, and the measuring accuracy of the blood pressure value can be improved.

Note that, in the operation description of FIG. 6, in step S12, amplitude of a first pulse wave detected after start of measurement was also used for blood pressure determination. However, the pace change amount of the compression in relation to the preceding beat cannot be calculated for this pulse wave. Because of this, even in the case where the change pace of the compression of the cuff 30 during the period of that pulse wave is not constant, the amplitude error of the pulse wave cannot be corrected.

With that, by cutting the amplitude of the pulse wave detected first after start of measurement out of the amplitude used at the time of blood pressure determination, blood pressure measurement accuracy can be further improved.

Also, although the change pace of the compression during the pulse wave period is changing at the threshold value or above in relation to the preceding pulse wave, by also, in the same way, cutting the pulse wave for which the change pace is not changing at the threshold value or above in relation to the following wave out of the amplitude used at the time of blood pressure determination, blood pressure measurement accuracy can be further improved. The reason for this is described below.

Figure 7:
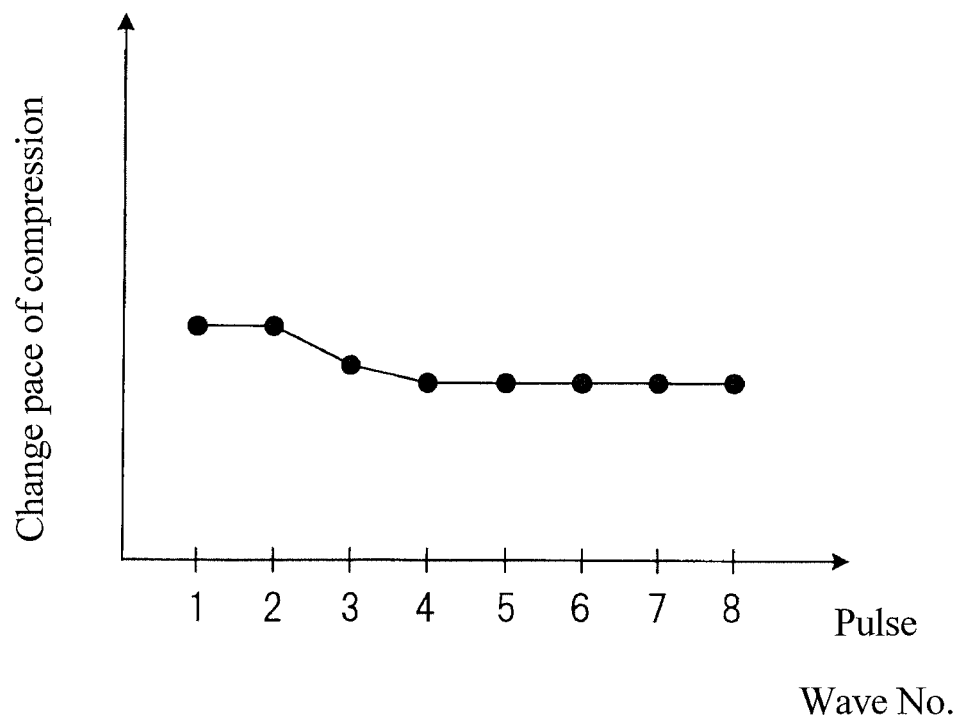
FIG. 7 is a diagram illustrating a relationship between eight pulse waves detected after measurement start and the change pace of the compression of each wave during the period of each pulse wave.

FIG. 7 is a diagram illustrating a relationship between eight pulse waves (pulse waves No. 1-8) detected after blood pressure measurement start and the change pace of the compression of each wave during the period of each pulse wave. In FIG. 7, there is a change in the change pace of the compression between pulse waves No. 2 and No. 3 that is equal to or exceeding the threshold value, and there is a change in the change pace of the compression between pulse waves No. 3 and No. 4 that is equal to or exceeding the threshold value.

In this case, if the operation described in FIG. 6 is followed, the amplitude for pulse waves No. 3 and No. 4 will be corrected.

Figure 8:
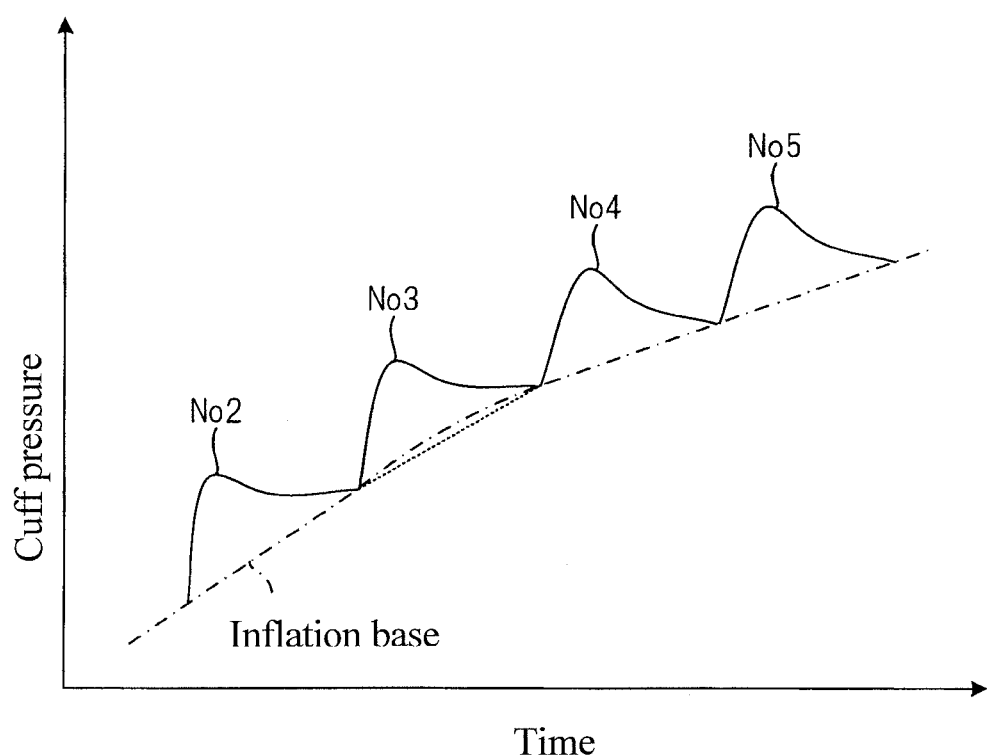
FIG. 8 is a diagram illustrating wave forms of pulse waves No. 2, No. 3, No. 4, and No. 5.

For example, the waveforms No. 2, No. 3, No. 4, and No. 5 illustrated in FIG. 7 are those illustrated in FIG. 8. Because the straight lines connecting the pulse wave rising point to the rising point of the following pulse wave in pulse waves No. 2, No. 4 and No. 5 coincide with the waveform of the dashed line illustrating the change of compression, error in amplitude does not occur.

On the other hand, because the straight line connecting the pulse wave rising point to the rising point of the following pulse wave in pulse wave No. 3 (the dotted line in FIG. 8) does not coincide with the waveform of the dashed line illustrating the change of compression, error in amplitude occurs.

In other words, in the case where cuff pressure like that illustrated in FIG. 8 is obtained, it is acceptable to correct only the amplitude of pulse wave No. 3 where the change pace of the compression in relation to the preceding and following pulse waves is changing equal to or in excess of the threshold value.

Because of this, although the change pace of the compression during the pulse wave period is changing at the threshold value or above in relation to the preceding pulse wave, by cutting the pulse wave for which the change pace is not changing at the threshold value or above in relation to the following wave (pulse wave No. 4 of FIGS. 7 and 8) out of the amplitude used at the time of blood pressure measurement, though amplitude correction will be done, blood pressure measurement accuracy can be further improved.

Note that correction of amplitude for pulse wave No. 4 of FIGS. 7 and 8 is omitted, and according to one or more embodiments of the present invention, the amplitude for which correction was not performed is included in the amplitude used at the time of blood pressure determination. As such, a reduction in the number of amplitude samples used for blood pressure determination can be avoided, and blood pressure determination accuracy can be improved.

Even if the amplitude of the first wave detected after measurement start and the amplitude of pulse wave No. 4 illustrated in FIGS. 7 and 8, or the corrected value thereof, are used in blood pressure determination, because the amplitudes of the other pulse waves can obtain precise values, it is possible to adequately raise an accuracy of blood pressure measurement.

Next, the improvement effect of blood pressure measurement accuracy through the blood pressure measurement device 1 is described based on experimental data.

Figure 9A:
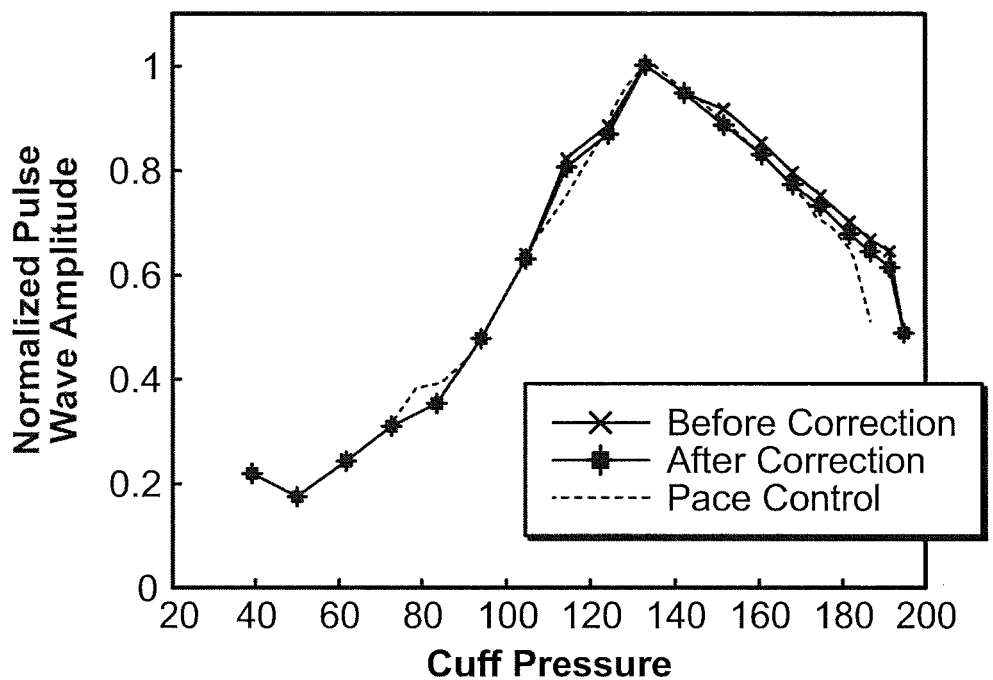
FIGS. 9A and 9B are diagrams describing an improvement effect of blood pressure measurement accuracy through the blood pressure measurement device 1.
Figure 9B:
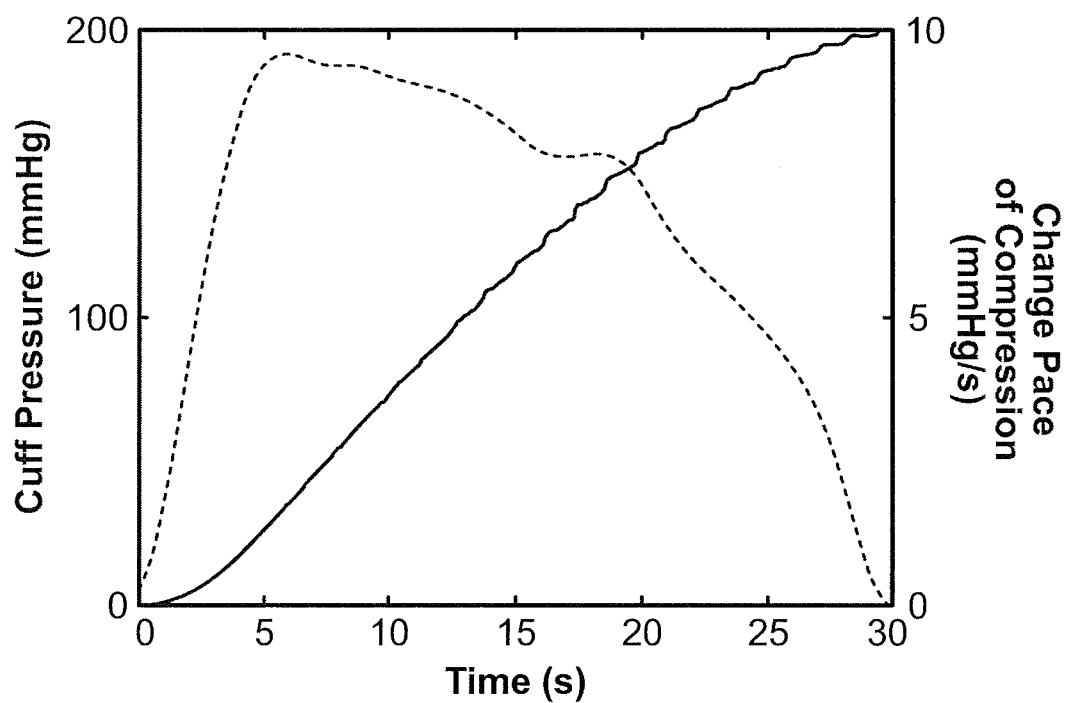
Figure 10:
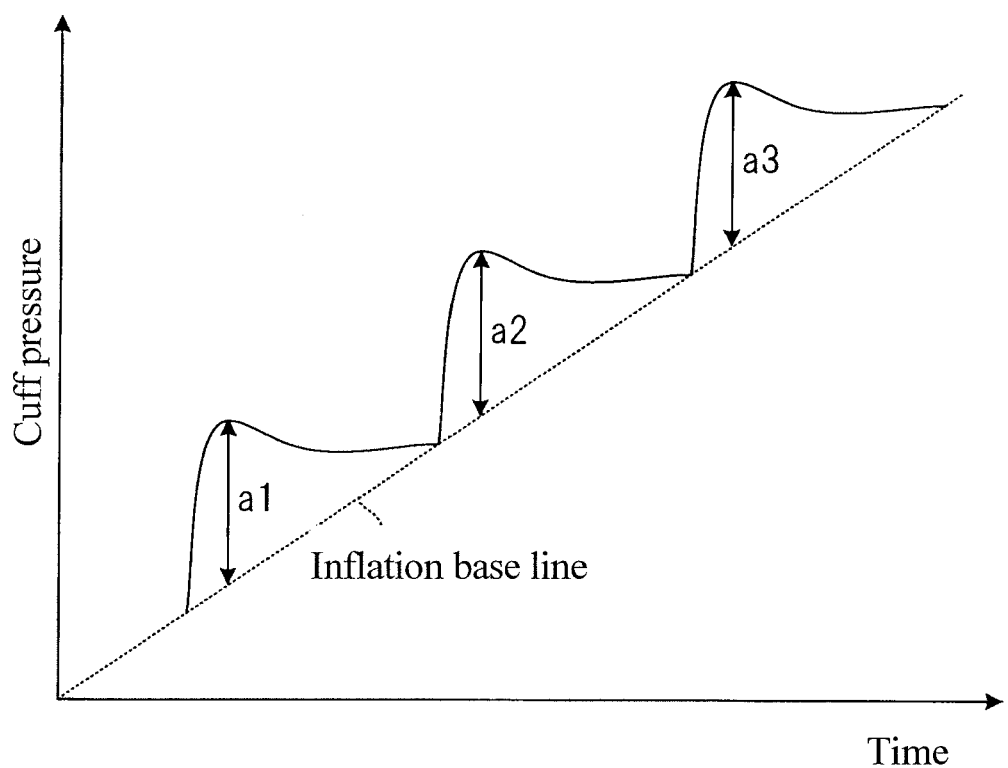
FIG. 10 is a diagram illustrating a change in detected cuff pressure during a period where the compression from the cuff is being increased by a basic oscillometric type blood pressure measurement device.

FIGS. 9A and 9B are diagrams describing an improvement effect of blood pressure measurement accuracy through the blood pressure measurement device 1. FIG. 9B is a graph illustrating compression of the cuff and the cuff pressure detected during the change period of this compression. In FIG. 9B the wave form illustrated by the broken line illustrates compression and the wave form illustrated by the solid line illustrates cuff pressure.

FIG. 9A is a graph illustrating the result of calculating an amplitude for each of the pulse waves with a method described in FIG. 6 from the cuff pressure illustrated in FIG. 9B.

The thick solid line illustrated in FIG. 9A illustrates the result in the case where the amplitude of each pulse wave is corrected with the method described in FIG. 6. The thin solid line illustrated in FIG. 9A illustrates the result in the case where the amplitude of each pulse wave is not corrected. Note that, the broken line in FIG. 9A illustrates calculated amplitude in a case where the compression of the cuff is controlled at a constant level in the entire period and where correction of amplitude is not performed.

As illustrated in FIGS. 9A and 9B, by putting into execution an amplitude correction process described in this embodiment, even in a case where the change pace of the compression of the cuff is not constant as illustrated in FIG. 9B, amplitude that is close to that in the case where the change pace of the compression of the cuff is controlled at a constant level can be obtained, and it is understood that blood pressure measurement accuracy can be improved.

It is possible to implement the function implemented in this embodiment by the CPU 18 through a general-purpose computer.

For example, a configuration using a unit that includes a configuration other than the CPU 18, display part 19 the operation part 21 and the memory 22 of FIG. 2 externally attached to a computer with a display part and an operation part connected is also acceptable.

In this configuration, the unit is controlled from the computer, and the computer, by performing the processing of step S3-step S12 illustrated in FIG. 6 using a signal sent from the unit, is able to implement the same function as the blood pressure measurement device 1 of this embodiment.

Also, a blood pressure measurement method performed by the CPU 18 of this embodiment can be provided as a program. This type of program is recorded to a permanent non-transitory recording medium from which the computer is able to read the program.

This type of "computer-readable recording medium" includes, for example, optical media, such as a Compact Disc-ROM (CD-ROM) and the like and magnetic recording media, such as a memory card and the like. Also, this type of program can also be provided by being downloaded through a network.

In the above, an embodiment applying a method for determining the amplitude of a pulse wave from the cuff pressure detected in a process that increases the compression through the cuff 30 is described. However, even if by a method for determining the amplitude of a pulse wave from the cuff pressure detected in a process that increases and decreases compression through the cuff 30, one or more embodiments of the present invention are applicable in the same way.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An oscillometric type sphygmomanometer, comprising:
   a cuff for wrapping around a measurement location of a patient;
   a pump and a valve that inflate/deflate the cuff;
   a pressure sensor that measures a cuff pressure on the measurement location during inflation/deflation of the cuff;
   a central control unit stored in a body of the sphygmomanometer that controls measurement of blood pressure, the central control unit comprising:
      a memory that stores a program and data to enable the central control unit to perform a predetermined operation;
      a cuff pressure detection section that receives a cuff pressure measured by the pressure sensor;
      a discrimination section that detects pulse waves that are synchronized with a pulse rate of the patient and superimposed on the cuff pressure;
      a pulse rate calculation section that calculates the pulse rate based on an interval between the pulse waves detected by the discrimination section;
      a pulse wave amplitude calculation section that:
         detects a rising time t0 of a pulse wave, a rising time t1 of a following pulse wave, and a cuff pressure t0$p$ and a cuff pressure t1$p$ at the rising times t0 and t1, respectively;
         detects a time ta when the pulse wave reaches a peak between time t0 and t1 and a cuff pressure M1 at the time ta;
         draws a straight line between (t0, t0$p$) and (t1, t1$p$) on an x-y coordinate system in which the x coordinate represents time and the y coordinate represents a cuff pressure value, and determines a position coordinate (ta, M2) on the straight line; and
         calculates an amplitude of the pulse wave between time t0 and t1 based on a difference between M1 and M2;
      a pace change calculation section that calculates an amount of change of an increasing/decreasing pace of the cuff pressure between the pulse waves based on a difference between the increasing/decreasing pace of the cuff pressure during a period of the pulse wave and the increasing/decreasing pace of the cuff pressure during a period of a preceding pulse wave;

a pulse wave amplitude correction section that corrects the amplitude of the pulse wave based on the amount of change of the increasing/decreasing pace of the cuff pressure calculated by the pace change calculation section and the pulse rate calculated by the pulse rate calculation section in accordance with a predetermined method; and a blood pressure determination section that determines a blood pressure value based on the amplitude of the pulse wave corrected by the pulse wave amplitude correction section.

2. The oscillometric type sphygmomanometer according to claim 1, wherein the memory stores a threshold value of the amount of change of the increasing/decreasing pace of the cuff pressure, and the pulse wave amplitude correction section corrects the amplitude of the pulse wave only when the amount of change of the increasing/decreasing pace of the cuff pressure exceeds a threshold value between the pulse waves.

3. The oscillometric type sphygmomanometer according to claim 1, wherein the pressure sensor is a capacitive type pressure sensor.

4. The oscillometric type sphygmomanometer according to claim 1, wherein the discrimination section detects the pulse waves that are synchronized with the pulse rate of the patient and superimposed on the cuff pressure by a filter processing.

5. The oscillometric type sphygmomanometer according to claim 1, wherein the pulse wave amplitude correction section corrects the amplitude of the pulse wave based on an amplitude error calculated in accordance with the following formula:

Amplitude error=($\alpha \times$ pulse rate+$\beta$)×change amount of pace, wherein $\alpha$ represents a coefficient experimentally obtained from a relationship between a value obtained by deducting the amplitude error from the increasing/decreasing pace of the cuff pressure and the pulse rate, and wherein $\beta$ represents a value obtained by deducting the amplitude error from the increasing/decreasing pace of the cuff pressure at a minimum pulse rate.

6. The oscillometric type sphygmomanometer according to claim 1, wherein the pace change calculation section detects the cuff pressure during each pulse wave by sampling pulse waves at predetermined time intervals and calculates the increasing/decreasing pace of the cuff pressure at the time intervals, and calculates a mean value of the increasing/decreasing pace of the cuff pressure as an increasing/decreasing pace of the cuff pressure during the period of the pulse waves.

7. A method of measuring a blood pressure by using an oscillometric type sphygmomanometer, comprising:

wrapping a cuff comprising a pressure sensor around a measurement location of a patient;

inflating and deflating the cuff;

detecting a cuff pressure on the measurement location during inflation/deflation of the cuff;

detecting pulse waves that are synchronized with a pulse rate of the patient and superimposed on the cuff pressure;

calculating the pulse rate based on an interval between the detected pulse waves;

detecting a rising time $t0$ of a pulse wave, a rising time $t1$ of a following pulse wave, and cuff pressures $t0p$ and $t1p$ at the rising time $t0$ and $t1$, respectively, and detecting a time $ta$ when the cuff pressure of the pulse wave reaches a peak between $t0$ and $t1$ and a cuff pressure M1 at the time $ta$;

drawing a straight line between ($t0$, $t0p$) and ($t1$, $t1p$) on an x-y coordinate system in which the x coordinate represents time and the y coordinate represents a cuff pressure value, and determining a position coordinate ($ta$, M2) on the straight line;

calculating an amplitude of the pulse wave based on a difference between M1 and M2 on the straight line, calculating an amount of change of an increasing/decreasing pace of the cuff pressure between the pulse waves based on a difference between the increasing/decreasing pace of the cuff pressure during a period of the pulse wave and the increasing/decreasing pace of the cuff pressure during a period of a preceding pulse wave;

correcting the amplitude of the pulse wave based on the amount of the detected increasing/decreasing pace of the cuff pressure and the pulse rate in accordance with a predetermined method; and determining a blood pressure value based on the corrected amplitude of the pulse wave.

8. The method according to claim 7, wherein a pulse wave amplitude correction section corrects the amplitude of the pulse wave only when the amount of change of the increasing/decreasing pace of the cuff pressure exceeds a predetermined threshold value between the pulse waves.

* * * * *